(12) United States Patent
Triva

(10) Patent No.: US 9,504,452 B2
(45) Date of Patent: Nov. 29, 2016

(54) PROCESS FOR REALISING A DEVICE FOR COLLECTING AND TRANSFERRING SAMPLES FOR MOLECULAR BIOLOGY

(75) Inventor: Daniele Triva, Brescia (IT)

(73) Assignee: Copan Italia S.p.A., Brescia (IT)

( * ) Notice: Subject to any disclaimer, the term of this patent is extended or adjusted under 35 U.S.C. 154(b) by 412 days.

(21) Appl. No.: 13/043,175

(22) Filed: Mar. 8, 2011

(65) Prior Publication Data
US 2012/0171712 A1   Jul. 5, 2012

(30) Foreign Application Priority Data

Jan. 5, 2011   (IT) .............................. MI2011A0004

(51) Int. Cl.
| | | |
|---|---|---|
| *C12Q 1/02* | (2006.01) | |
| *G01N 1/18* | (2006.01) | |
| *B01D 21/00* | (2006.01) | |
| *A61B 10/00* | (2006.01) | |
| *A61B 10/02* | (2006.01) | |
| *B01L 3/00* | (2006.01) | |
| *G01N 1/02* | (2006.01) | |

(52) U.S. Cl.
CPC ........ *A61B 10/0045* (2013.01); *A61B 10/0096* (2013.01); *A61B 2010/0216* (2013.01); *B01L 3/5029* (2013.01); *G01N 2001/028* (2013.01); *Y10T 436/25375* (2015.01)

(58) Field of Classification Search
None
See application file for complete search history.

(56) References Cited

U.S. PATENT DOCUMENTS

| | | |
|---|---|---|
| 3,163,160 A | 12/1964 | Cohen |
| 3,434,801 A | 3/1969 | Scherr |
| 3,744,499 A | 7/1973 | Wells |
| 3,792,699 A | 2/1974 | Tobin et al. |
| 3,854,319 A | 12/1974 | Burroughs et al. |
| 3,888,629 A | 6/1975 | Bagshawe |
| 3,900,651 A | 8/1975 | Hoppe et al. |

(Continued)

FOREIGN PATENT DOCUMENTS

| | | |
|---|---|---|
| CN | 1070850 | 4/1993 |
| CN | 2183735 | 11/1994 |

(Continued)

OTHER PUBLICATIONS

Leemans et al., Evaluation of methodology for the isolation and analysis of LCN-DNA before and after dactyloscopic enhancement of fingerprints, 2006, Elsevier, pp. 583-585.*

(Continued)

*Primary Examiner* — Jill Warden
*Assistant Examiner* — Julie Tavares
(74) *Attorney, Agent, or Firm* — Fish & Richardson P.C.

(57) ABSTRACT

A process for realizing a device (1) for collecting and transferring samples for molecular biology, the device including at least: a support body (2) having at least a first portion (2a), and a plurality of fibers (6) attached and arranged on the first portion (2a) of the support body (2) by flocking, such as to define a flocked collecting portion (3) destined to collect, on the said collecting portion, (3) a quantity of the sample for molecular biology, the process including at least a step of pre-treating the plurality of fibers (6) with a surfactant, the step of pre-treating the plurality of fibers (6) with a surfactant being performed after application of the fibers on the support body (2) by flocking and/or before application of the fibers (6) on the body (2) by flocking and/or wherein the surfactant is added to the fiber (6) during production of the fiber (6).

17 Claims, 2 Drawing Sheets

(56) References Cited

U.S. PATENT DOCUMENTS

| | | | |
|---|---|---|---|
| 3,954,563 A | 5/1976 | Mennen | |
| 4,030,978 A | 6/1977 | Abramson | |
| 4,039,934 A | 8/1977 | Ostashko et al. | |
| 4,175,560 A | 11/1979 | Knoll | |
| 4,196,167 A | 4/1980 | Olsen | |
| 4,234,316 A | 11/1980 | Hevey | |
| 4,307,152 A | 12/1981 | Mathes et al. | |
| 4,326,545 A | 4/1982 | Motegi et al. | |
| 4,340,670 A | 7/1982 | Mennen | |
| 4,371,485 A | 2/1983 | Mathes et al. | |
| 4,421,809 A * | 12/1983 | Bish et al. | 428/90 |
| 4,525,452 A * | 6/1985 | Jones | C12Q 1/10 435/29 |
| 4,612,147 A | 9/1986 | Haubold et al. | |
| 4,707,450 A | 11/1987 | Nason | |
| 4,719,181 A | 1/1988 | Schobel et al. | |
| 4,734,964 A | 4/1988 | Lane et al. | |
| 4,749,655 A | 6/1988 | Corasaniti et al. | |
| 4,754,764 A | 7/1988 | Bayne | |
| 4,767,398 A | 8/1988 | Blasius, Jr. | |
| 4,796,647 A | 1/1989 | Gueret | |
| 4,861,343 A | 8/1989 | Neunzig | |
| 4,877,036 A | 10/1989 | Saint-Amand | |
| 4,877,037 A | 10/1989 | Ko et al. | |
| 4,922,936 A | 5/1990 | Buzzi et al. | |
| 4,953,560 A | 9/1990 | Samuels | |
| 4,974,980 A | 12/1990 | Gueret | |
| 5,009,846 A | 4/1991 | Gavet et al. | |
| 5,022,408 A | 6/1991 | Mohajer | |
| 5,091,153 A | 2/1992 | Bachand | |
| 5,163,441 A | 11/1992 | Monthony et al. | |
| 5,279,964 A | 1/1994 | Chrisope | |
| 5,324,128 A | 6/1994 | Gueret | |
| 5,370,992 A * | 12/1994 | Shah | C12Q 1/689 435/6.15 |
| 5,418,136 A * | 5/1995 | Miller | G01N 33/54373 250/458.1 |
| 5,460,781 A | 10/1995 | Hori | |
| 5,468,606 A * | 11/1995 | Bogart | B82Y 15/00 356/369 |
| 5,538,732 A | 7/1996 | Smith et al. | |
| 5,614,375 A | 3/1997 | Citri | |
| 5,623,941 A | 4/1997 | Hedberg et al. | |
| 5,627,071 A | 5/1997 | Triva | |
| 5,676,643 A | 10/1997 | Cann et al. | |
| 5,704,388 A | 1/1998 | Freeman | |
| 5,710,041 A | 1/1998 | Moorman et al. | |
| 5,738,643 A | 4/1998 | Stredic, III | |
| 5,846,215 A | 12/1998 | Zygmont | |
| 5,899,622 A | 5/1999 | Gueret | |
| 5,928,176 A | 7/1999 | Nakatani | |
| 5,944,519 A | 8/1999 | Griffiths | |
| 6,010,462 A | 1/2000 | Stoermer, III | |
| 6,033,143 A | 3/2000 | Gueret | |
| 6,080,126 A | 6/2000 | Zygmont | |
| 6,232,567 B1 | 5/2001 | Bonino et al. | |
| 6,286,246 B1 | 9/2001 | Rachal et al. | |
| 6,341,912 B1 | 1/2002 | Gueret | |
| 6,352,513 B1 | 3/2002 | Anderson et al. | |
| 6,365,794 B1 | 4/2002 | Dabi et al. | |
| 6,413,087 B1 | 7/2002 | Petrich et al. | |
| 6,420,181 B1 | 7/2002 | Novak | |
| 6,450,810 B1 | 9/2002 | Fischer et al. | |
| 6,451,607 B1 | 9/2002 | Lawrence et al. | |
| 6,494,856 B1 | 12/2002 | Zygmont | |
| 6,503,013 B2 | 1/2003 | Strauss | |
| 6,541,194 B2 | 4/2003 | DiCesare | |
| 6,676,609 B1 | 1/2004 | Rutenberg et al. | |
| 6,732,743 B1 | 5/2004 | Bouix et al. | |
| 6,881,554 B2 * | 4/2005 | DiCesare et al. | 435/30 |
| 6,887,681 B2 | 5/2005 | DiCesare et al. | |
| 7,022,289 B1 | 4/2006 | Schlein et al. | |
| 7,198,623 B2 | 4/2007 | Fischer et al. | |
| 7,582,067 B2 | 9/2009 | Van Acker | |
| 7,645,608 B2 | 1/2010 | Greene | |
| 8,114,027 B2 | 2/2012 | Triva | |
| 8,133,193 B2 | 3/2012 | Van Acker | |
| 8,317,728 B2 | 11/2012 | Triva | |
| 8,772,034 B2 | 7/2014 | Rasch-Menges et al. | |
| 2002/0001539 A1 | 1/2002 | DiCesare et al. | |
| 2002/0197738 A1 | 12/2002 | Matsumoto et al. | |
| 2003/0073932 A1 | 4/2003 | Varey | |
| 2003/0108846 A1 | 6/2003 | Hoertsch | |
| 2004/0014063 A1 | 1/2004 | Batteux et al. | |
| 2004/0078219 A1 | 4/2004 | Kaylor et al. | |
| 2004/0158188 A1 | 8/2004 | Kauffmann et al. | |
| 2004/0197730 A1 | 10/2004 | Rowe et al. | |
| 2005/0181517 A1 | 8/2005 | Chandler et al. | |
| 2005/0223511 A1 | 10/2005 | Mangold et al. | |
| 2005/0223512 A1 | 10/2005 | Mangold et al. | |
| 2005/0267395 A1 | 12/2005 | Mangold et al. | |
| 2005/0288616 A1 * | 12/2005 | Bozenbury et al. | 604/1 |
| 2006/0115805 A1 | 6/2006 | Hansen et al. | |
| 2006/0142668 A1 * | 6/2006 | Triva | 600/572 |
| 2006/0211978 A1 | 9/2006 | Do | |
| 2006/0258250 A1 | 11/2006 | Mangold et al. | |
| 2007/0105186 A1 | 5/2007 | Gibson et al. | |
| 2007/0208274 A1 | 9/2007 | Ostrowski et al. | |
| 2007/0255175 A1 * | 11/2007 | Sangha | A61B 10/0045 600/572 |
| 2007/0275101 A1 * | 11/2007 | Lu et al. | 424/719 |
| 2009/0024060 A1 * | 1/2009 | Darrigrand et al. | 600/584 |
| 2009/0030054 A1 | 1/2009 | Warmington et al. | |
| 2009/0030341 A1 | 1/2009 | Kshirsagar et al. | |
| 2009/0186057 A1 | 7/2009 | Farmer et al. | |
| 2009/0325861 A1 | 12/2009 | Goodheart | |
| 2010/0249649 A1 | 9/2010 | Larkin | |
| 2011/0281754 A1 | 11/2011 | Fischer et al. | |
| 2011/0306078 A1 | 12/2011 | Triva | |
| 2012/0150088 A1 | 6/2012 | Triva | |
| 2012/0271196 A1 | 10/2012 | Triva | |
| 2013/0072817 A1 | 3/2013 | Triva | |
| 2013/0338535 A1 | 12/2013 | Triva | |

FOREIGN PATENT DOCUMENTS

| | | |
|---|---|---|
| CN | 2460050 | 11/2001 |
| CN | 2479505 | 2/2002 |
| CN | 2554995 | 6/2003 |
| CN | 201131761 | 10/2008 |
| CN | 101765551 | 6/2010 |
| CN | 201993241 | 9/2011 |
| DE | 2552172 A1 | 6/1977 |
| DE | 2755341 A1 | 6/1977 |
| DE | 2552172 B2 | 9/1977 |
| DE | 298 09 833 U1 | 6/1998 |
| DE | 10246379 A1 | 4/2004 |
| EP | 0 223 745 | 5/1987 |
| EP | 0354823 | 2/1990 |
| EP | 0 244 156 B1 | 4/1990 |
| EP | 0 568 556 A1 | 7/1995 |
| EP | 0693263 | 1/1996 |
| EP | 0 707 836 A2 | 4/1996 |
| EP | 1 147 746 | 10/2001 |
| EP | 1 358 818 A1 | 11/2003 |
| EP | 1382730 | 1/2004 |
| EP | 1608268 | 11/2007 |
| EP | 2395337 | 12/2011 |
| FR | 2729545 | 7/1996 |
| GB | 406850 A | 3/1934 |
| JP | 05-027671 | 4/1993 |
| JP | 10-192050 | 7/1998 |
| JP | 11-514849 | 12/1999 |
| JP | 2000-152817 | 6/2000 |
| JP | 2000232982 A2 | 8/2000 |
| JP | 2000342591 | 12/2000 |
| JP | 2001-346626 | 12/2001 |
| JP | 2002067201 | 3/2002 |
| JP | A-2004-587 | 1/2004 |
| JP | 2007139556 | 7/2007 |
| WO | WO 89/10724 | 11/1989 |
| WO | WO 9212863 | 8/1992 |
| WO | WO97/03209 | 1/1997 |
| WO | WO 00/09984 | 2/2000 |

(56) References Cited

FOREIGN PATENT DOCUMENTS

| WO | WO 00/54024 | 9/2000 |
| WO | WO 2004/086979 | 10/2004 |
| WO | 2005013759 | 2/2005 |
| WO | 2005110316 | 11/2005 |
| WO | WO 2007/075412 | 7/2007 |
| WO | WO 2008/131033 | 10/2008 |
| WO | 2009018607 | 2/2009 |
| WO | 2009140356 | 11/2009 |
| WO | WO 2009/134509 | 11/2009 |
| WO | WO 2009/136892 | 11/2009 |
| WO | WO 2009/158403 | 12/2009 |

OTHER PUBLICATIONS

Print of website in English http://www.flock.de/pages/html/de/flock/sub/historie.html.

BG Information, Translation of p. 7 of BGI 764 from http://babelfish.yahoo.com/translate_txt, Oct. 2000, including translation from Babel Fish.

Print of Website www.swicofil.com/flock.html, verified by "Internet Archive" that the print of this website is of Aug. 16, 2002.

BG-Information, BGI 764, p. 7, Oct. 2000.

Daniele Triva, "Swab for Collecting Biological Specimens" U.S. Appl. No. 10/543,873, filed Jul. 28, 2005.

Daniele Triva, "Swab for Collecting Biological Specimens" U.S. Appl. No. 12/903,921, filed Oct. 13, 2010.

Daniele Triva, "Method for Quantitative Transfer of Analytes" U.S. Appl. No. 12/840,087, filed Jul. 20, 2010.

Applied Biosystems, Benchmarking of applicators, Dec. 19, 2006, 26 pages.

Verhoeven et al. Better Detection of *Staphylococcus aureus* Nasal Carriage by Use of Nylon Flocked Swabs, JCM, vol. 48, No. 11, Nov. 2010; 3 pages.

Chernesky et al. Use of Flocked Swabs and a Universal Transport Medium to Enhance Molecular Detection of Chlamydia trachomastis and Neisseria gonorrhoeae; JCM, vol. 44, No. 3, Mar. 2006, 3 pages.

Hedin et al., New Technique to Take Samples from Environmental Surfaces Using Flocked Nylon Swabs; Journal of Hospital Infection 75 (2010); 4 pages.

Moore et al. Dry Cotton or Flocked Respiratory Swabs as a Simple Collection Technique for the Molecular Detection of Respiratory Viruses Using Real-Time NASBA, JVM 153 (2008) 6 pages.

Wurmb-Schwardk, "Fast and Simply DNA Extraction from Saliva and Sperm Cells Obtained from the Skin or Isolated from Swabs", Elsevier—Legal Medicine, Mar. 2006, 6 pages.

"Safety Data Sheet in Accordance with Regulation 453/2010", Jun. 6, 2011, 6 pages.

Thomasma, "A39 Optimization of Touch DNA Collection Techniques Using Alternative Swabbing Solutions", Proceedings American Academy of Forensic Sciences, XP055163017, Apr. 2010, pp. 40-41, 4 pages.

Thomasma, "The Influence of Swabbing Solutions on DNA Recovery from Touch Samples", Journal of Forensic Sciences, vol. 58, No. 2, Mar. 2013, 6 pages.

Communication pursuant to Article 94(3) EPC, European Application No. 12703153.2, Jan. 29, 2015, 7 pages.

PCT International Search Report and Written Opinion of the International Searching Authority, PCT/IB2012/050018, Mar. 5, 2012, 11 pages.

Chinese First Office Action, Chinese Application No. 201280004723.8, Sep. 29, 2014, 14 pages. (Statement of Relevance included in Information Disclosure Statement).

Chinese Second Office Action, Chinese Application No. 20120004723.8, May 18, 2015, 11 pages. (Statement of Relevance included in Information Disclosure Statement).

Office Action, Federal Service for Intellectual Property, Russia, Nov. 2015, 5 pages.

Japanese Office Action, Japanese Application No. 2013-547945, Oct. 2015, 7 pages.

European Communication Pursuant to Article 94(3) EPC, European Application No. 12703153.2, Sep. 15, 2015, 4 pages.

Japanese Patent Office, Summarized English Translation of Notice of Reasons for Rejection, Jun. 21, 2016, 4 pages.

"Flock 2003" Int. Flock Symposium, Apr. 2003, Dresden (3 pages).

Cotton—Facts and General Information from Swicofil, http:/lwww.swicofil.com/products/001cotton.html, Jan. 3, 2011, (9 pages).

Cotton—Wikipedia, the free encyclopedia, http://en.\wikipedia.org/wiki/Cotton, Jan. 3, 2011 (12pages).

MicroRheologics, "New Technology for Sample Collection" 2006, (2 pages).

Millipore, "Flocked Swabs" 2007, (2 pages).

What is Cotton Fibre/Properties of Cotton Fiber, http://articles.textileclass.com/cotton-fibre-what-is-cotton-fibre-cotton-f, May 11, 2011, (1 page).

Wikipedia, "Cotton Swab" http//en.wikipedia.org/wiki/Cotton swab, Jun. 22, 2011 (3 pages).

Wikipedia, "Swab" http://en.wikipedia.org/wiki/Swab, Jun. 22, 2011 (1 page).

* cited by examiner

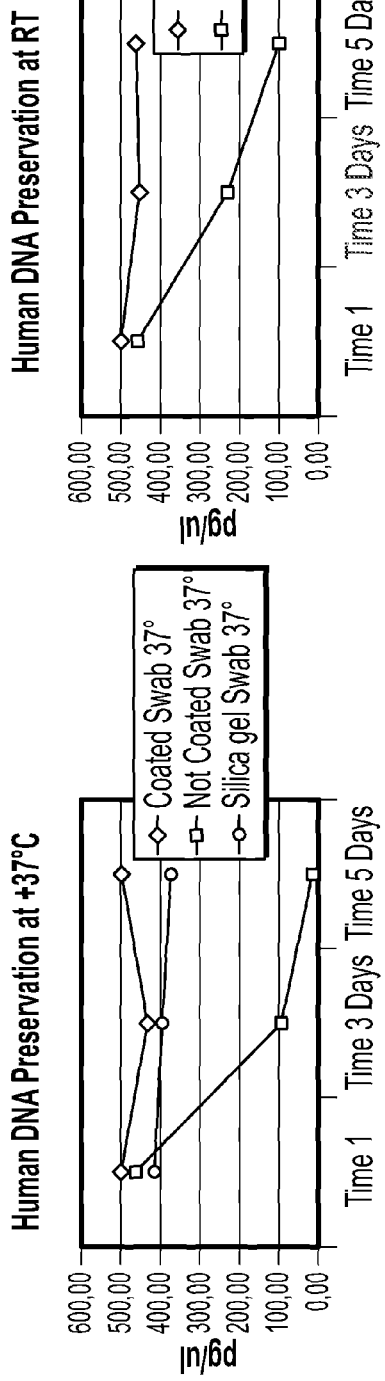
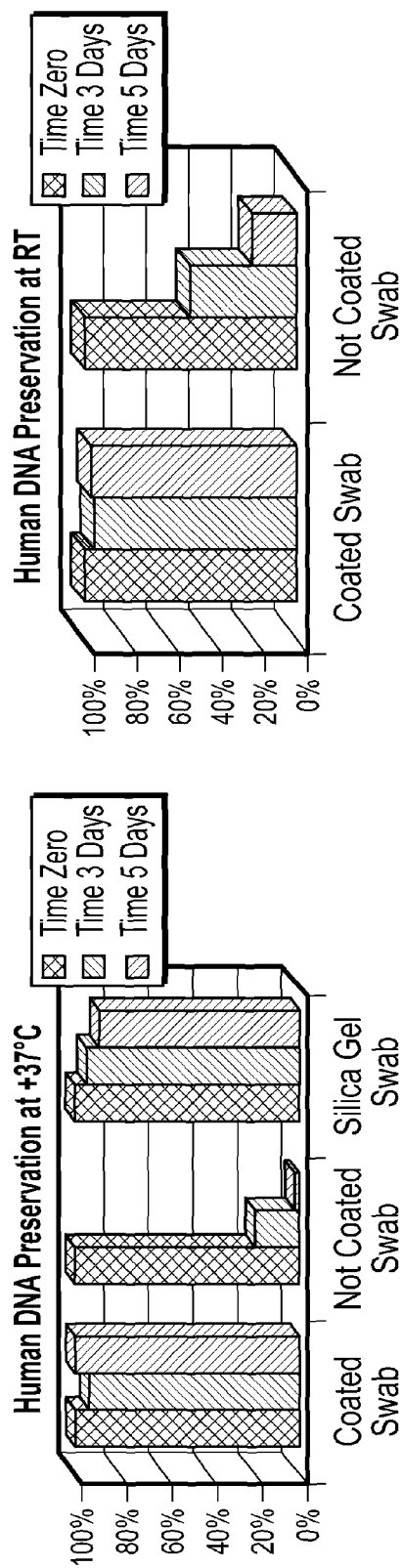
FIG. 4A
FIG. 4B
FIG. 4C
FIG. 4D

PROCESS FOR REALISING A DEVICE FOR COLLECTING AND TRANSFERRING SAMPLES FOR MOLECULAR BIOLOGY

CROSS-REFERENCE TO RELATED APPLICATIONS

The present application claims priority under 35 U.S.C. §119 to Italian Patent Application No. MI2011A000004, filed Jan. 5, 2011, the entirety of which is hereby incorporated by reference.

BACKGROUND

The present invention relates to a process for realising a device for collecting and transferring samples for molecular biology.

The invention also relates to a device for collecting and transferring samples for molecular biology realised using the process and a method for collecting and transferring samples for molecular biology by using the device.

The invention is, for example, applicable for collecting and transferring samples for molecular biology, such as DNA, RNA and cells containing DNA and RNA.

The invention can further be usefully applied for collecting and transferring other types of analytes or biological samples or samples of biological origin.

The prior art includes various types of devices for collecting and transferring analytes such as organic or biological substances, for example to be subsequently subjected to laboratory examinations of analytic or diagnostic type. The prior art especially describes the use of conventional collecting devices comprising an elongate support body and an elongate fibre, generally cotton, wound about an end of the body, up to defining a collecting portion destined to absorb internally thereof the samples to be collected.

These devices exhibit various drawbacks, among which is the fact that the biological samples tend to be retained inside the collecting portion, and thus are difficult to extract from the collecting portion when necessary. Thus the quantity of sample that can be recuperated from the initially-available sample is often very limited, which results in numerous drawbacks. As in some cases the actual quantity of substance collected can be very limited in the first place, it is of fundamental importance to be able to collect the greatest possible percentage of initially-collected substance. To obviate this drawback, devices have been provided, conventionally known as flocked swabs and comprising an elongate support body and a plurality of flocked fibres at an end of the support body such as to define a collecting portion for the analytes or biological samples. The fibres can be flocked on the body by flocking in a magnetic field, and can adhere to the support body with an appropriate glue or even without the use of adhesives. The fibres can be arranged orderly and substantially perpendicular to the support body, such as to define an optimal configuration for collection, transport and selective release of the collected samples. This type of device is known, for example, from a patent belonging to the present applicant, EP1608268 B1. Thanks to the ordered arrangement of the fibres parallel to the support body, these devices are able to absorb quantities of analytes or samples that are at least equivalent to conventional devices as described above, but exhibit the big advantage of enabling release, at the appropriate moment, of much larger quantities of the analytes or samples from the collected portion, with up to 80% or even more of the original sample easily salvaged. The applicant has found that although the above-described flocked devices can be advantageously used also for collecting and transferring samples for molecular biology such as DNA, RNA and cells containing these samples, the quantities of DNA and RNA release by the device and effectively usable for performing molecular biology operations, such as polymerisation or amplification, are sometimes unsatisfactory or insufficient, with all the consequent difficulties of the case in performing processes to be performed on the samples.

SUMMARY

The main aim of the present invention is to resolve one or more of the problems encountered in the prior art. An aim of the present invention is to provide a method and a device for collecting and transferring samples for molecular biology which enable extracting from the collecting device a greater quantity of samples for molecular biology usable for operations of molecular biology, with respect to known devices. A further aim of the present invention is to provide a method and a device for collecting and transferring the samples for molecular biology which enable extracting from the collecting device the greatest possible percentage of DNA or RNA initially collected by the device, in the best form and conditions for all further uses. A further aim of the invention is to provide a method and a device for collecting and transferring samples for molecular biology which enables effectively conserving the integrity of the DNA or RNA samples collected by the device. A further aim of the present invention is to provide a method and a device for collecting and transferring samples for molecular biology which enable a reduction in the number of cycles necessary for performing the polymerisation reactions or the chain reactions of the polymerase on the DNA or RNA samples released by the device. A further aim of the present invention is to provide a method and a device for collecting and transferring samples for molecular biology which are simple and economical to realise. These aims and others besides, which will more fully emerge from the following description, are substantially attained by a method and a device for collecting and transferring samples for molecular biology, and by a process for realising a device for collecting and transferring samples for molecular biology, according to what is set out in one or more of the accompanying claims, taken alone or in combination, or in any combination with more or more of the further aspects described herein below. In a further aspect, the invention further relates to a process in accordance with any one of the appended process claims, or with the further aspects indicated herein, further comprising at least a step of producing the support body of the device having at least the first portion and the step of applying, by flocking, the plurality of fibres on the first portion.

In a further aspect, the invention further relates to a process in accordance with any one of the appended process claims, or with the further aspects indicated herein, further comprising the step of drying the fibres following the step of pre-treating the fibres. In a further aspect, the invention further relates to a process in accordance with any one of the appended process claims, or with the further aspects indicated herein, in which the surfactant is cationic or benzalkonium chloride (BAC or alkyl-dimethyl-benzylammonium chloride or ADBAC) and in which the fibres are made of nylon. In a further aspect, the invention further relates to a device for collecting and transferring samples for molecular biology realised with a process for realising a device for collecting and transferring samples for molecular biology in accordance with any one of the appended claims. In a further aspect, the invention further relates to a method according to any one of the appended method claims, or the further aspects indicated herein, in which the stage of predisposing the solution comprises steps of predisposing a predetermined quantity of surfactants, preferably cationic; dissolving the predetermined quantity of surfactants in water in order to obtain the solution, and/or the step of making the solution substantially homogeneous. In a further aspect, the invention further relates to a method according to any one of the appended method claims, or the further aspects indicated herein, further comprising the step of drying at least the collecting portion provided by the sample and/or further comprising the steps of inserting the collecting portion in a hermetic container, during the step of drying or independently of the step of drying. In a further aspect, the invention further relates to a method according to any one of the appended method claims, or the further aspects indicated herein, further comprising the step of releasing at least 80%, or at least 86%, or at least 90%, or at least 95% of the collected sample from the collecting portion, for example by dilution in liquid medium, suspension in a buffer or a buffer solution. In a further preferred aspect thereof, the invention further relates to the use of a surfactant or a cationic surfactant for pre-treating fibres applied or to be applied by flocking on a support body of a device for collecting and transferring samples for molecular biology, in order to increase a quantity of DNA or RNA releasable by the collecting device and usable for operations of molecular biology with respect to a quantity releasable and usable for operations of molecular biology obtainable from fibres of the device which have not be pre-treated. In a further preferred aspect thereof, the invention further relates to the use of a cationic surfactant, in particular benzalkonium chloride, for pre-treating nylon fibres applied or to be applied by flocking on a support body of a collecting and transferring device of samples for molecular biology, in order to increase the DNA or RNA percentage usable for operations of molecular biology with respect to the releasable quantity by the collecting and transferring device. In a further aspect, the invention further relates to the use of a cationic surfactant for the production of fibres to be applied by flocking on a support body of a collecting and transferring device of samples for molecular biology, in which the cationic surfactant is added to materials with which the fibres are realised during the production of the fibres. A detailed description is now provided, by way of non-limiting example, of one or more preferred embodiments of the invention, with the aid of the figures of the drawings.

DESCRIPTION OF DRAWINGS

FIGS. 4A-4D are graphs and charts representing the trend of the human DNA preservation on the swabs at the 2 different temperatures tested.

DETAILED DESCRIPTION

Figure 1:
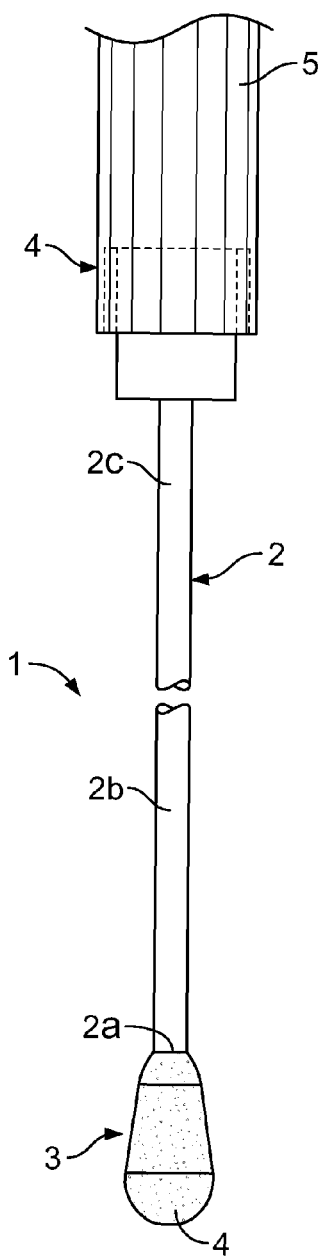
FIG. 1 is a lateral view of a device according to an embodiment of the present example.
Figure 2:
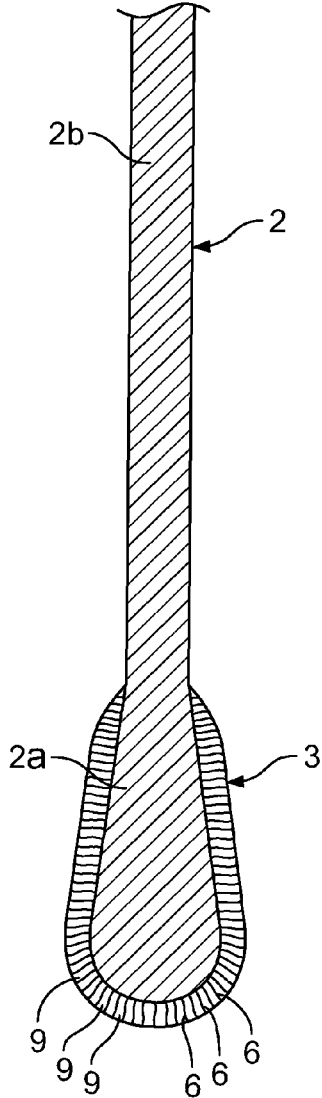
FIG. 2 is a view of a detail of the device of FIG. 1 relating to a collecting portion
Figure 3:
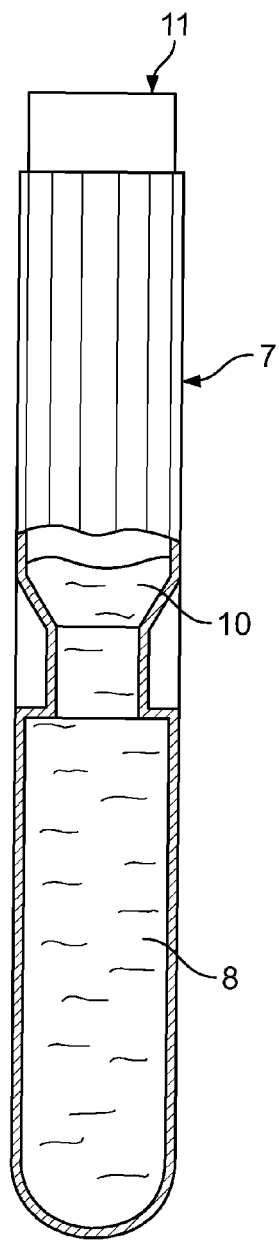
FIG. 3 is a container according to an embodiment of the present invention.

There now follows a description of a collecting and transferring device 1 of samples for molecular biology in accordance with one or more embodiments of the invention. In the present text, the term "molecular biology" is intended to mean the techniques that enable detection, analysis, manipulation, amplification (PCR) and copying (cloning) nucleic acids (DNA and RNA).

The expression "DNA or RNA usable for molecular biology operations" is intended to mean that the DNA or RNA is integral, not damaged or rendered unusable and in any case is in sufficiently good conditions for the performing of various molecular biology operations, for example polymerisation reactions.

With reference to the accompanying figures of the drawings, 1 denotes in its entirety a device for collecting and transferring samples for molecular biology. The device 1 comprises a support body 2 which can have an elongate conformation and/or substantially a rod-like conformation. The support body 2 can have any section, including a variable one along a longitudinal extension thereof. The support body is provided with a first portion 2a, for example an end portion, defining a collecting portion 3 for the sample, a central second portion 2b, substantially rod-shaped, and an end third portion 2c, at which it can be manually gripped by an operator or can be connected to a further gripping element 4 such as a cap 5 for test tubes or the like.

The collecting portion 3 for the sample can be conformed as a swab. The collecting portion 3 is flocked, realised by flocking of a plurality of fibres 6 on the first end 2a of the body. The fibres 6 flocked on the first end can be made of hydrophilous or non-hydrophilous material, but the collecting portion 3 is in any case hydrophilous by capillary effect thanks to the characteristics of the fibres 6 and the distribution thereof on the support body 2. The flocked fibres 6 are preferably made of nylon. In other words, the collecting portion 3 can exhibit a continuous layer of fibres 6 made of a substantially adsorbent or non-absorbent material towards the sample, but conformed in an ordered plurality of capillary interstices 9 in which a predetermined quantity of the sample, for example a liquid sample, can be retained by imbibition, and from which the sample can be quantitatively released at the appropriate moment, for example by rubbing of the collecting portion 3 on a special release surface. An example of this type of flocked swab is illustrated in patent EP1.608.268 belonging to the present applicant, the contents of which that relate to the structure of the flocked swab are incorporated by reference in the present description. As described in the above-mentioned patent, depositing by flocking produces, on the involved end of the collecting device 1, a continuous and homogeneous layer of a plurality of fibres 6 having an ordered arrangement, substantially perpendicular at every point of the first portion 2a of the support body 2 and each of which is substantially parallel to the adjacent fibres 6. A corresponding ordered plurality of capillary interstices 9 is defined between the fibres 6, and it is between these a predetermined quantity of the sample is collected and retained, possibly by imbibition due to the capillary effect. The flocked layer can thereafter effectively release the collected sample, for example by rubbing on a special surface or by dilution of the sample in an appropriate diluent. The flocked collecting portion 3 can be configured and dimensioned such as to collect an appropriate quantity of sample, or to collect a quantity of sample comprised for example between 5 and 1000 microliters, between 10 microliters and 500 microliters or between 50 and 200 microliters, or between 80 and 120 microliters. The fibres 6 can be arranged on the support body 2 in a substantially ordered way and in such a way as to form a substantially continuous layer on the collecting portion 3 and/or can be arranged on the collecting portion 3 in such a way as to define a plurality of capillary interstices 9 destined to adsorb the liquid sample by capillary action. The fibres 6 can exhibit a yarn count comprised between 1 and 10 Dtex, or preferably between 1.7 and 3.3 Dtex, and/or the fibres 6 can exhibit a length comprised between 0.6 and 3 mm. The fibres 6 can be arranged by flocking on the collecting portion 3 of the support body 2 with a surface density comprised for example between 50 and 500 fibres per mm$^2$ or between 100 and 200 fibres per mm$^2$ of surface of the first portion 2a of the support body 2. The layer of fibres can define an absorbance capacity for example of at least 0.5 µl per mm$^2$, or at least 0.6 µl per mm$^2$, or at least 0.7 µl per mm$^2$, or at least 0.75 µl per mm$^2$ of surface of the support body 2. The fibres 6 can be made of a material that is substantially not hydrophilous or not adsorbent of the sample, and/or of a material that is substantially hydrophilous or adsorbent of the sample and/or in a material selected from: polyamide, nylon, rayon, polyester, carbon fibre, alginate, natural fibre, or a mixture of the cited materials. The fibres are preferably made of nylon. The support body 2 can exhibit a longitudinal extension comprised between 2 cm and 20 cm, or between 3 cm and 18 cm, or between 6 cm and 16 cm and/or a thickness or diameter in a section that is perpendicular to the central axis thereof, comprised between 0.5 mm and 5 mm, or between 1 mm and 3 mm, or between 1.5 and 2.5 mm. The collecting portion 3 can exhibit a longitudinal extension comprised between 8 cm and 0.5 cm or between 5 cm and 1 cm and/or a diameter or thickness, including the fibres 6, between 10 mm and 1 mm or between 8 mm and 2 mm or between 5 mm and 2.5 mm. The collection portion 3 can exhibit any shape suitable for the type of sample to be collected or suitable for the collection seating, for example rounded or with one or more live edges. The support body 2 can be provided with an intermediate weakened portion destined to facilitate a selective breaking of the body itself in an intermediate position between the first end and the second end, for example in order to facilitate insertion of the collecting portion 3 into a container 7 for transport. The collection device 1 can comprise a plurality of support bodies 2, each provided with a collecting portion 3 having a conformation or shape that is different and specifically configured for collecting a sample in a specific seating, or for collecting a specific quantity of sample. In the present invention, the fibres 6 are pre-treated before use for collecting the sample, and for example during the production stage of the device 1, with a surfactant. The surfactant might be cationic, anionic, non-ionic or amphoteric. In the present invention, the surfactant is preferably cationic. In the invention, the use of a cationic surfactant, for example and in particular benzalkonium chloride, enables the above-described aims to be attained in a way which is surprising and particularly significant. In the invention, the use of a cationic surfactant, for example and in particular benzalkonium chloride, enables the above-described aims to be attained in a way which is surprisingly and particularly significant in use with nylon fibres. In the invention, the cationic surfactant is preferably benzalkonium chloride (BAC or alkyl-dimethyl-benzylammonium chloride or ADBAC). The cationic surfactant can be a salt having a positive part, constituted by at least a chain of carbon atoms with a quaternary ammonia group and/or can be a quaternary ammonia salt or can comprise a mixture of ammonia salts. The cationic surfactant can be a mixture of chlorides of alkyl-benzyl-dimethyl ammonium, in which the alkyl group varies from octile ($C_8H_{17}$—) to octadecyl ($C_{18}H_{37}$—). In an alternative embodiment the cationic surfactant could be cetyltrimethyl ammonium bromide (CTAB or hexadecyl trimethyl ammonium bromide). In further alternative embodiments the cationic surfactant may be for example benzethonium chloride, cetalkonium chloride, laurtrimonium bromide, myristyltrimethylammonium bromide, cetrimide, cetrimonium bromide, cetylpyridinium chloride or stearalkonium chloride. The collecting device 1 can further comprise a container 7 for transport of the sample having an internal containment seating 10 and an access opening 11. The container 7 can be a test tube for transport of samples of biological material or of biological origin. The collecting device 1 can further comprise a closing cap 5, removably mountable at the access opening for selectively closing the container 7. The collecting device 1 can further comprise at least a drying or dehumidifying element, for example a bag containing silicone gel, housed in the container 7 or in another useful position. The container 7 and/or the closing cap 5 and/or the support body 2 can be made of a plastic material, for example polystyrol or polystyrene or polypropylene and/or in a material suitable for use with the specific sample to be collected, or in general suited to use with biological materials or materials of biological origin. The container 7 and/or the closing cap 5 and/or the support body 2 can be sterilised. The collection device 1 can further comprise a sealed packaging (not illustrated in the figures as of known type) in which the support body 2 and/or the container 7 and the closing cap 5 can be housed before use for collecting a sample. The support body 2, the packing, the container 7 and the cap 5 can be sterile. The invention further relates to a process for realising a device 1 for collecting and transferring samples for molecular biology of the above-described type. The process can comprise, for example, the following steps, in themselves of known type and therefore not described in greater detail: realising the support body 2, for example by extrusion of a plastic material; applying a suitable glue to the first portion 2a of the body 2; applying the fibres 6 to the first portion 2a by means of flocking in an electromagnetic field; drying the glue in an appropriate kiln of conventional type in order at least partially to polymerise the glue. In the present invention, the process further comprises the step of pre-treating the plurality of fibres 6 with a cationic surfactant, of the above-described type. The process can further comprise a drying step of the fibres, for example in a kiln, at least after the step of pre-treating the fibres. The step of pre-treating the plurality of fibres 6 with a cationic surfactant can be performed after application of the fibres on the support body 2 by flocking, and it can be done by directly immersing the collecting portion in a solution containing the cationic surfactant. Alternatively, the step of pre-treating the plurality of fibres 6 with the above-cited cationic surfactant can be performed before application of the fibres 6 on the body by flocking, thus treating the fibres 6 before the flocking thereof. In a further alternative the cationic surfactant can be added to the fibres 6 during production of the fibre 6, adding a predetermined quantity of cationic surfactant to the materials of known type with of the fibre is made. The process can further comprise the step of predisposing a water-based solution comprising a percentage, a concentration value or a quantity of the surfactant, preferably cationic, in the solution of from 0.1% to 15%, or from 0.2% to 10%, or from 0.5% to 5%, or from 0.8% to 1.5% or from 0.4% to 1.2% in volume or in weight. For example a preferred concentration is from 0.4 grams of benzalkonium chloride per 100 ml of solution to 1.2 gram per 100 ml of solution. The same preferred concentration can apply to other cationic surfactants. The step of predisposing the solution can comprise steps of predisposing a predetermined quantity of cationic surfactant; dissolving the predetermined quantity of cationic surfactant in water or watery solution in order to obtain the solution, and/or the step of making the solution substantially homogeneous. The step of treating the plurality of fibres 6 with a cationic surfactant can be performed by imbibition of the fibres in the solution. The imbibition of the fibres 6 in the solution can be performed after application of the fibres on the collecting portion of the body by flocking or before the application of the fibres on the collecting portion of the body by flocking. The invention further relates to a method for collecting and transferring samples for molecular biology by means of a device 1 of the above-described type. The method comprises at least the step of collecting a sample for molecular biology on at least a flocked collecting portion 3 of the collecting device 1, in which the plurality of fibres 6 is pre-treated with a cationic surfactant of the above-described type. The method can be used for collecting and transferring DNA or RNA samples, and/or cells comprising samples of DNA or RNA. The method can also comprise the step of conserving the sample on the collecting portion 3 for predetermined period of time. The method can also comprise the step of dehydrating or drying at least the collecting portion 3, provided with the collected sample. The step of drying can be performed, for example, by means of drying in a forced-ventilation oven, or by another method of known type and suitable for treatment of the sample.

The method can further comprise steps of inserting the collecting portion 3 in a vacuum container (of known type and therefore not illustrated in the figures) and substantially generating a vacuum in the vacuum container. The step of generating a vacuum can be performed during the step of drying, or in another moment, separately from the step of drying. The method can further comprise a step of rehydrating the sample on the collecting portion 3, for example with at least a hydrating solution, in order to obtain a predetermined quantity of rehydrated sample on the collecting portion 3. The method can further comprise steps of inserting the collecting portion 3, containing the sample, in a container 7 such as for example a test tube, closing the container 7 with a cap 5 or closing cover and transferring the container 7 comprising the collecting portion 3 and/or the step of predisposing in the container 7 a predetermined quantity of a substance 8 destined to liquefaction and/or conserving the sample and/or the step of jogging, shaking or rotating the container 7 comprising the collecting portion 3 with the sample at a predetermined velocity aimed at liquefying the sample. The method can further comprise a step of releasing the sample for molecular biology from the collecting portion in order to enable molecular biology operations on the sample. The method can in particular comprise a step of releasing at least 80%, or at least 85%, or at least 90% of the quantity of the collected sample for molecular biology, by dilution in a liquid medium or a dilution buffer in order to enable further operations on the sample to be performed. The release can be facilitated by means of conventional rubbing operations. The invention further relates to the use of a cationic surfactant, of the above-indicated type, for pre-treating fibres 6 applied or to be applied by flocking on a support body 2 of a collecting device and transferring samples for molecular biology. Hereinafter we will report the results of tests carried out by treating a flocked swab having flocked nylon fibers, treated with a solution with a concentration of about 1 gram of benzalkonium chloride per 100 ml of liquid.

To simulate the DNA collection on crime scene, 100 ul of sterile demineralized water was used to re-moisten saliva spots (that had previously been dried on a hard surface to reproduce DNA collection on a crime scene), each one of which was collected with a single swab. The average concentrations and the percentages of recovered DNA were calculated. Different kind of swabs were tested: not coated (not treated) flocked nylon fiber swabs and coated (treated) nylon fiber swabs. During the tests, the optimization of the DNA preservation on the swab, also in critical environmental conditions, was studied. In particular the test valued the correct preservation of the sample on the swab once it has been collected, for example from a crime scene, until its arrival to the forensic laboratory. Two tests were carried out:

1) In order to verify the ability of coated flocked swabs to maintain the DNA collected on the crime scene, saliva was inoculated on the swabs and the DNA was extracted and quantified in Real Time PCR at time zero and after 1 week at room temperature.

The following table shows the percentage of DNA recovered from the coated swabs at different times (at time zero, after 24 hours, after 48 hours and after 1 week):

| Coated Swab: time point of testing | DNA concentration (ng/ul) | Percentage of DNA recovery (%) |
|---|---|---|
| time zero | 1.70 ng/ul | 100 |
| time 24 hours | 1.68 ng/ul | 99 |
| time 48 hours | 1.69 ng/ul | 100 |
| time 1 week | 1.67 ng/ul | 98 |

2) To simulate a crime scene collection in presence of great quantity of environmental contaminants and to simulate a swab's transport in critical temperature conditions (for example in summer time or in very hot areas), where temperatures changes and consequent contaminants' overgrowth could be a real problem to human DNA conservation on the swab, another test has been done inoculating every swab with 100 ul of 0.5 McF mix of environmental contaminant agents and human saliva. The DNA from every swab was extracted and quantified in Real Time PCR at time zero, at time 3 days at Room Temperature (RT) and at +37° C., at time 5 days at Room Temperature and at +37° C. The graphs in FIGS. 4A-4D represent the trend of the human DNA preservation on the swabs at the 2 different temperatures tested.

As regards the number of cycles necessary for Real Time PCR, coated swabs required, in the different conditions tested, a number of cycles from a minimum of about 27.27 (at time zero) to a maximum of about 27.27 (after 5 days at 37° C.), while non-coated swabs required a number of cycles from a minimum of 27.38 (at time zero) to a maximum of about 33.33 (after 5 days at 37° C.). The above test demonstrates that coated swabs are able to preserve about 100% of collected DNA also after 5 days, not only at room temperature (optimized condition) but also at critical incubation's temperature (+37° C.), without the necessity to dry the swab using silica gel devices, and to improve by up to 100 times the test sensitivity, in comparison with a not coated swab. The present invention provides one or more of the following advantages. First and foremost, the invention enables a process and a device realised in accordance with the process, and a method for using the device, which obviate the problems encountered in the prior art. The invention further enables a relevant quantity of samples (in relation to the quantity collected) for molecular biology, such as DNA or RNA, to be extracted from the collecting device, and in particular enables the samples to be conserved more carefully and in better integral conditions with respect to the prior art; thus any subsequent use in the laboratory is made possible. The invention enables an increase in the percentage of DNA or RNA usable for molecular biology operations involving collection and transfer, with respect to the prior art. This is possible thanks to the ability of the treatment to conserve the integrity of the human cells and avoid their lyse, maintaining consequently the nucleic acids integrity too. In addition to what above, the present invention may be advantageously used also for collection of other biological or chemical samples to be analyzed. The invention further allows to collect, to transfer and to make available for analysis and for further operations a major quantity of biological sample with respect to known devices. The invention enables quantities of DNA or RNA to be made available and usable for performing operations of molecular biology, which quantities are significantly greater, even by up to tenfold, with respect to known devices. The invention further enables a reduction in the number of cycles required for performing polymerisation reactions or polymerase chain reactions on samples of DNA or RNA released by the device, as it enables releasing, from the collecting device, a greater quantity of DNA or RNA available for these operations. Finally, the invention is simple and economical to realise.

A number of embodiments of the invention have been described. Nevertheless, it will be understood that various modifications may be made without departing from the spirit and scope of the invention. Accordingly, other embodiments are within the scope of the following claims.

What is claimed is:

1. A method for collecting, conserving and transferring samples of DNA or RNA for molecular biology, the method comprising:
    collecting a sample of DNA or RNA for molecular biology on at least a flocked collecting portion (3) of a collecting device (1) having a support body (2), the collecting portion (3) comprising a first portion (2a) of the support body (2) and a plurality of fibres (6) attached and arranged on the first portion (2a) of the support body (2) by flocking;
    conserving the integrity of the DNA or RNA samples collected by the device sufficiently to enable subsequent use of said samples in laboratory examinations of analytic or diagnostic type, wherein the sample is conserved and preserved on the collecting portion for a predetermined period of time of at least twenty-four hours; and
    releasing the sample of DNA or RNA for molecular biology from the collecting portion (3) in order to enable performance of operation of molecular biology on the sample; and
    wherein conserving comprises pretreating the plurality of fibres (6) with a surfactant, wherein the surfactant is a mixture of chlorides of alkyl-benzyl-dimethyl ammonium, in which the alkyl group varies from octile ($C_8H_{17}$—) to octadecyl ($C_{18}H_{37}$—), wherein the pretreated plurality of fibers (6) conserve the integrity of the DNA or RNA samples collected by the device on said collecting portion during said predetermined period of time.

2. The method of claim 1 wherein said step of conserving the sample is carried out by conserving the sample on the flocked collecting portion (3) for a period of time of at least forty-eight hours.

3. The method of claim 1 wherein said step of conserving the sample is carried out by conserving the sample on the flocked collecting portion (3) for a period of time of at least three days.

4. The method of claim 1 wherein said step of conserving the sample is carried out by conserving the sample on the flocked collecting portion (3) for a period of time of at least five days.

5. The method of claim 1 wherein said step of conserving the sample is carried out by conserving the sample on the flocked collecting portion (3) for a period of time of at least one week.

6. The method of claim 1, wherein the flocked collecting portion (3) collects a substantially known quantity of the sample or collects a quantity of between 5 and 1000 microliters, or between 10 microliters and 500 microliters, or between 50 and 200 microliters, or between 80 and 120 microliters of the sample and/or collects a quantity of sample of at least 0.5 µl per $mm^2$, or at least 0.6 µl per $mm^2$, or at least 0.7 µl per $mm^2$, or at least 0.75 µl per $mm^2$.

7. The method of claim 1, comprising: arranging the fibres (6) on the first portion (2a) of the support body (2) in a substantially ordered way and to form a substantially continuous layer on the collecting portion (3) and/or arranging the fibres (6) on the collecting portion (3) in such a way as to define a plurality of capillary interstices (9) destined to absorb the sample by capillary action.

8. The method of claim 1, comprising arranging the fibres (6) with a yarn count of between 1.7 and 3.3 Dtex, and/or a length of between 0.6 and 3 mm.

9. The method of claim 1, comprising arranging the fibres (6) made of at least one of nylon or of a material selected from: polyamide, rayon, polyester, carbon fibre, alginate, natural fibre.

10. The method of claim 1, comprising collecting the sample of DNA or RNA for molecular biology on said collecting portion (3) exhibiting a surface density of the fibres (6) on the collecting portion (3) of between 50 and 500 fibres per $mm^2$ or between 100 and 200 fibres per $mm^2$.

11. A method for performing operations of molecular biology on a sample, comprising: performing the method for collecting, conserving and transferring samples of DNA or RNA for molecular biology according to claim 1; and performing operations of molecular biology on the sample.

12. The method of claim 11, performing polymerisation reactions or chain reactions of the polymerase on the DNA or RNA samples released.

13. The method of claim 1, further comprising the step of drying at least the collecting portion (3) provided with the sample.

14. The method of claim 13, wherein the step of drying is performed by drying in a forced-ventilation oven.

15. The method of claim 1, further comprising the step of inserting the collecting portion (3) in a hermetic container during the step of drying.

16. A method for collecting, conserving and transferring samples of DNA or RNA for molecular biology, the method comprising:
    collecting a sample of DNA or RNA for molecular biology on at least a flocked collecting portion (3) of a collecting device (1) having a support body (2), the collecting portion (3) comprising a first portion (2a) of the support body (2) and a plurality of fibres (6) attached and arranged on the first portion (2a) of the support body (2) by flocking, said collecting portion (3) exhibiting a surface density of the fibres (6) on the collecting portion (3) of between 50 and 500 fibres per $mm^2$ or between 100 and 200 fibres per $mm^2$;
    conserving the integrity of the DNA or RNA samples collected by the device sufficiently to enable subsequent use of said samples in laboratory examinations of analytic or diagnostic type, wherein the sample is conserved and preserved on the collecting portion for a predetermined period of time of at least twenty-four hours; and releasing the sample of DNA or RNA for molecular biology from the collecting portion (3) in order to enable performance of operation of molecular biology on the sample; and wherein conserving comprises pretreating the plurality of fibres (6) with a surfactant, wherein the pre-treated plurality of fibers (6) conserve the integrity of the DNA or RNA samples collected by the device on said collecting portion during said predetermined period of time.

17. A method for collecting, conserving and transferring samples of DNA or RNA for molecular biology, the method comprising:

collecting a sample of DNA or RNA for molecular biology on at least a flocked collecting portion (3) of a collecting device (1) having a support body (2), the collecting portion (3) comprising a first portion (2a) of the support body (2) and a plurality of fibres (6) attached and arranged on the first portion (2a) of the support body (2) by flocking;

conserving the integrity of the DNA or RNA samples collected by the device sufficiently to enable subsequent use of said samples in laboratory examinations of analytic or diagnostic type, wherein the sample is conserved and preserved on the collecting portion for a predetermined period of time of at least twenty-four hours; and releasing the sample of DNA or RNA for molecular biology from the collecting portion (3) in order to enable performance of operation of molecular biology on the sample; and wherein conserving comprises pretreating the plurality of fibres (6) with a surfactant, wherein the pre-treated plurality of fibers (6) conserve the integrity of the DNA or RNA samples collected by the device on said collecting portion during said predetermined period of time;

further comprising the step of drying at least the collecting portion (3) provided with the sample, wherein the step of drying is performed by drying in a forced-ventilation oven.

* * * * *